United States Patent

Nabai et al.

[11] Patent Number: 5,533,979
[45] Date of Patent: Jul. 9, 1996

[54] HYPODERMIC NEEDLE STEADY REST AND REMOVAL TOOL

[76] Inventors: Hossein Nabai, 14555 Levan Rd., Suite 410, Livonia, Mich. 48154; Homayoon Rahbari, 1314 N. Macomb St., P.O. Box 57, Monroe, Mich. 48161-0057

[21] Appl. No.: 204,058

[22] Filed: Mar. 1, 1994

[51] Int. Cl.$^6$ .................................................. A61M 5/00
[52] U.S. Cl. ........................ 604/187; 604/177; 604/242
[58] Field of Search ................................. 604/187, 188, 604/192, 238, 242, 177, 905; 128/770, 919; 206/364–366

[56] References Cited

U.S. PATENT DOCUMENTS

| | | | |
|---|---|---|---|
| 2,541,621 | 2/1951 | Thompson | 604/92 |
| 4,031,890 | 6/1977 | Homan | 604/187 X |
| 4,516,969 | 5/1985 | Kintner | 604/187 |
| 4,563,177 | 1/1986 | Kamen | 604/177 |
| 4,742,910 | 5/1988 | Staebler | 206/365 |
| 4,904,244 | 2/1990 | Harsh et al. | 604/187 |
| 4,909,788 | 3/1990 | Egolf | 604/187 |
| 5,305,766 | 4/1994 | Hahn | 604/192 |
| 5,338,309 | 8/1994 | Imbert | 604/187 |
| 5,342,311 | 8/1994 | Dirina | 604/116 |
| 5,451,214 | 9/1995 | Hajishoveh | 604/235 |

FOREIGN PATENT DOCUMENTS 0485028  5/1992  European Pat. Off. ............... 604/187

*Primary Examiner*—Randall L. Green
*Assistant Examiner*—V. Alexander
*Attorney, Agent, or Firm*—Alex Rhodes

[57] ABSTRACT

A thin blade shaped tool for the one-handed removal of a needle from an end of a syringe. The tool has an aperture in the center thereof for slideably mounting the tool on an end portion of the syringe, adjacent the needle, and sides extending outwardly from the syringe for a one-handed removal of said needle with a pair of fingers of a hand which holds the syringe. The sides have spaced apart ends and concave center portions for resting the syringe on a patient or IV line during an alignment of the needle with an injection site.

9 Claims, 2 Drawing Sheets

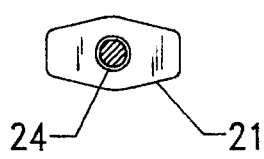
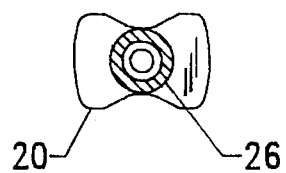
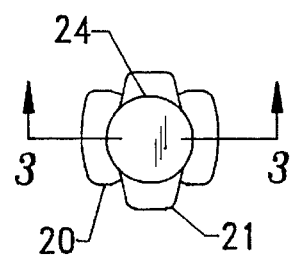
FIG. 5          FIG. 4          FIG. 1
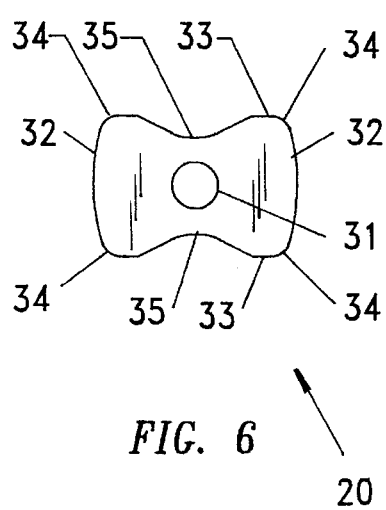
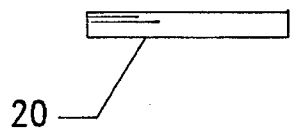
FIG. 6
FIG. 7
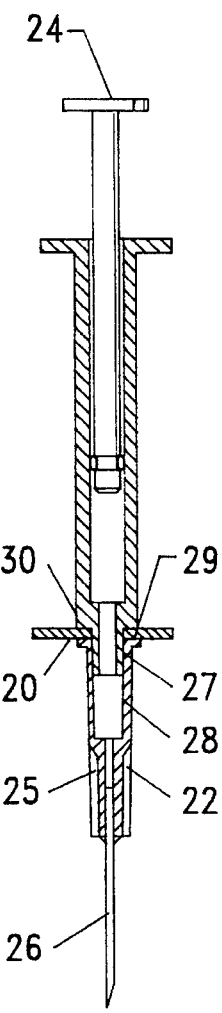
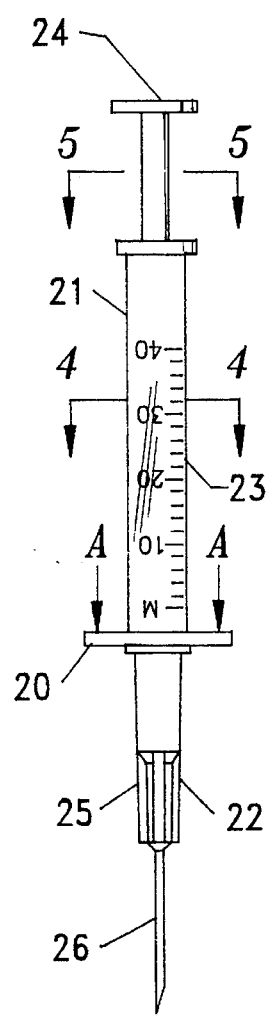
FIG. 3          FIG. 2

HYPODERMIC NEEDLE STEADY REST AND REMOVAL TOOL

FIELD OF INVENTION

This invention relates to surgical devices and more particularly to a hypodermic needle steady rest and removal tool.

BACKGROUND OF THE INVENTION

Many physicians, nurses and other medical workers are exposed, almost daily, to blood transmitted diseases, such as hepatitis and AIDS. Increased exposure to dangerous viral and bacterial diseases has expanded the need for devices to protect the health of medical workers.

One source of medical worker infection are accidental punctures with hypodermic needles. Accidental punctures may occur when discarded syringes and needles are mixed with discarded surgical bandages, pads and gauze. Accidental punctures may also occur during two-handed removals of needles from syringes.

Accidental punctures may also occur during injections of medications or the drawing of blood.

SUMMARY OF THE INVENTION

The present invention satisfies the foregoing need for increased safety by providing a simple, easy to use, tool for removing a needle from an end of a syringe. One important benefit of the invention is that it can be used with existing syringes and needles.

A feature of the invention is that a needle can be removed from a syringe with the same hand which holds the syringe. The one-handed procedure reduces the risk of puncturing the opposite hand.

Another benefit of the invention is that it serves as a steady rest during the alignment of a needle with a patient or an IV line.

The combined steady rest and tool is a thin, generally rectangular blade for mounting between a syringe and a needle which is mounted on the end of the syringe. When the blade is mounted between the needle and syringe, the sides of the blade extend outwardly of the syringe, whereby the needle can be removed by pressing the fingers of the same hand which holds the syringe against the blade.

Another feature of the invention is that the sides of the tool can be used to support a syringe on a patient or an IV line while aligning a needle.

Further features and benefits will become apparent from the ensuing description and accompanying drawings which describe the invention in detail. The best mode which is contemplated in practicing the invention is disclosed and the property in which exclusive rights are claimed is set forth in each of the numbered claims which are appended to the detailed description.

BRIEF DESCRIPTION OF THE DRAWINGS

FIG. 1 is a plan view of a syringe, needle and needle steady rest and removal tool in accordance with the invention.

FIG. 2 is a front view of FIG. 1.

FIG. 3 is a cross-sectional view taken on the line 3—3 in FIG. 1.

FIG. 4 is a cross-sectional view taken on the line 4—4 in FIG. 2.

FIG. 5 is a cross-sectional view taken on the line 5—5 of FIG. 1.

FIG. 6 is a plan view of only the needle removal tool drawn to an enlarged scale.

FIG. 7 is a front view of FIG. 6.

DETAILED DESCRIPTION OF THE PREFERRED EMBODIMENT

Figure 11:
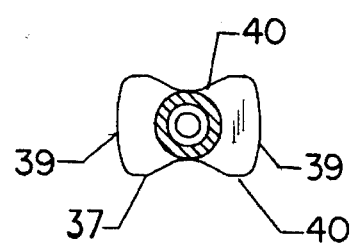
FIG. 11 is a cross-sectional view taken on the line 11—11 in FIG. 9.

Referring now to the drawings wherein like numerals designate like and corresponding parts throughout the several views, in FIGS. 1 through 5, inclusive, a hypodermic needle steady rest and removal tool, designated by the numeral 20, is shown mounted on a conventional syringe 21 and needle 22. The syringe 21 has a cylindrical body 23 and a plunger 24 slideably mounted in the body 23. The needle 22 consists of a molded housing 25 and a sharp pointed tubular member 26 pressed into the housing 25.

The end portion 27 of the syringe 21 on which the needle 22 is mounted is reduced and tapered. The tapered syringe end portion 27 is lightly press fitted into a tapered aperture 28 of the needle housing 25. When the tapered end portion 27 of the syringe 21 is pressed into the aperture 28 of the needle housing 25, a gap 29 is formed between the needle housing 25 and the adjacent cylindrical portion 30 of the syringe body 23.

The steady rest and removal tool 20 is preferably molded or die cut from a sheet of plastic. It is a thin retangular blade shaped part with an aperture 31 in the center thereof and sides 32, 33 extending outwardly from the syringe 21. The ends 34 of the sides 32, 33 are spaced apart to form steady rests for supporting the syringe 21 and needle 22 on a patient. The center portions 35 of sides 32 are concave for supporting the syringe 21 and needle 22 on an IV line (not shown).

The tool 20 is mounted on the syringe 21 by engaging the tool's aperture 31 with the tapered end 27 of the syringe 21 before the needle 22 is pressed on to the tapered end 21 of the syringe 21. The tool 20 is used in the following manner. Before a syringe 21 is discarded, if a needle 22 is mounted on the syringe 21, the needle 22 is removed by pressing the fingers of the hand which holds the syringe 21 against the blade shaped tool 20, in the direction of arrows "A". The pressure of the blade shaped tool 20 against the needle 21, forcibly separates the needle 22 from the end 27 of the syringe 21.

During an alignment of the needle 26 for the drawing of blood or injection of medication, the tool 20 is used to steady the needle 26 by resting one of the sides 32 or 33 of the tool 20 on a patient near the injection site. The needle assembly 26 is steadied on an IV line (not shown) by resting the concave portion 30 of one of the sides 32 on the IV line during an alignment of the needle 26 with an IV port.

Figure 8:
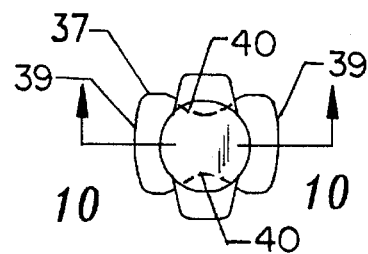
FIG. 8 is a plan view of an alternate embodiment of a syringe, needle and needle removal and alignment tool in accordance with the invention.
Figure 10:
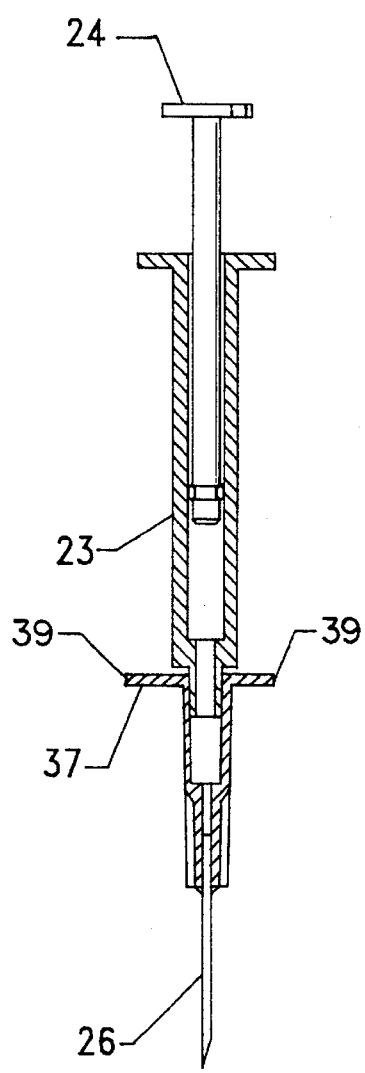
FIG. 10 is a cross-sectional view taken on the line 10—10 in FIG. 8.
Figure 9:
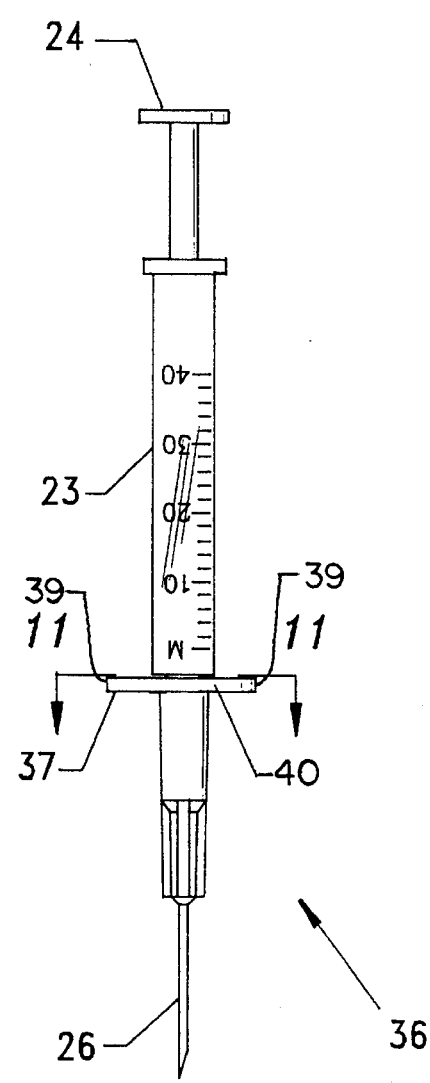
FIG. 9 is a front view of FIG. 8.

Referring now to FIGS. 8 through 11, inclusive, an alternate embodiment 36 is shown, wherein the tool 37 is molded integral with a needle 38 (not shown) as a flange having sides 39, 40 which extend outwardly from a syringe 41. The needle 42 is removed from the syringe 21 and steadied during an alignment with an injection site in the manner previously described for the first embodiment.

From the foregoing it will be understood that our invention improves safety by providing a simple, easy to use, one-handed tool and method which can be applied to remove a conventional needle as well as serving as a steady rest during the alignment of a needle with an injection site.

Although but two embodiments of our invention have been described, it is not our intention to limit our invention to these embodiments, since other embodiments can be derived by changes and substitutions known to those skilled in the art without departing from the spirit thereof.

We claim:

1. In combination, a syringe, said syringe having a cylindrical body portion and a tapered end portion; a needle removably mounted on said tapered end portion of said syringe; and a thin, generally rectangular, flat, blade shaped steady rest and needle removal tool slideably mounted on said tapered end portion of said syringe between said needle and said body portion of said syringe, said thin blade shaped tool being normal to an axis of said body of syringe and such that an edge of said tool as a steady rest and to align said needle having an aperture in the center thereof for slideably mounting said tool on said tapered end portion of said syringe, adjacent said needle, said tool having at least one side extending outwardly from said cylindrical body of said syringe which facilitates a one-handed pushing of said needle away from said end of said syringe by pressing fingers of a hand which holds said syringe in an axial direction against said outward extending side of said blade shaped tool, at least one of said sides being arcuate and extending outwardly from said cylindrical body portion of said syringe by an amount which is sufficient for supporting an edge of said rectangular shaped tool on a patient to align and steady said needle mounted on the end of said syringe with an injection site of said patient.

2. The combination recited in claim 1 wherein at least one of said sides for resting an edge of said tool on a patient has a concave portion for resting said edge of said side on an IV line during an alignment of said needle with an injection port of said IV line.

3. The combination recited in claim 1 wherein said generally rectangular blade shaped tool has at least one pair of opposite spaced apart sides extending outwardly from said syringe by an amount which is sufficient for resting an edge of either of said sides on a patient during an alignment of said needle with an injection site.

4. The combination recited in claim 1 wherein said generally rectangular blade shaped tool has two pairs of opposite sides and each of said sides has a concave center portion for resting an edge of either of said sides on an IV line to align said needle with a port of said IV line.

5. In combination, a syringe, said syringe having a cylindrical body portion and a tapered end portion; a needle detachably mounted on said tapered end portion of said syringe, said needle comprising a one-piece housing and a sharp pointed tubular member fixed to said housing; and a means which facilitates a one-handed pushing of said needle away from said syringe and to align said needle with an injection site of a patient, said means comprising: a generally thin flat rectangular flange portion of said needle's housing, said flange portion being normal to an axis of said needle and adjacent said body portion of said syringe and having at least one pair of spaced apart sides extending outwardly from said body of said syringe for enabling a user of said syringe to push said needle away from said syringe by pressing a pair of fingers of a hand which holds said syringe in an axial direction against said outward extending sides of said flange portion of said needle and for resting an edge of one of said outward extending sides on an IV line or a patient to align said needle with an injection site or a port of said IV line.

6. The combination recited in claim 5 wherein each of said sides has concave center portions for resting said syringe on a patient or IV line during an alignment of said needle with an injection site or a port of said IV line.

7. The combination recited in claim 5 wherein said generally rectangular flange portion of said needle has two pair of opposing sides and each of said sides has a concave portion for resting said syringe on a patient or an IV line during said alignment of said needle with said injection site or a port of said IV line.

8. In an apparatus comprised of a syringe and a needle detachably mounted to one end of said syringe, the improvement comprising: a thin generally rectangular blade shaped tool slideably mounted on said end of said syringe which facilitates the one-handed removal of said needle from said end of said syringe, said tool being normal to an axis of said needle and having an aperture in the center thereof for slideably mounting said tool on said end portion of said syringe adjacent said needle, said tool having two pairs of opposing sides extending outwardly from said syringe for a one-handed pushing of said needle away from said end of said syringe by pressing a pair of fingers of a hand which holds said syringe against a pair of said sides of said generally rectangular tool and supporting said syringe on a patient to align said needle with an injection site.

9. The blade shaped tool recited in claim 8 further comprising each of said sides having spaced apart ends and concave center portions for resting said syringe on a patient or an IV line during an alignment of said needle with an injection site of said patient or said IV line.

\* \* \* \* \*